United States Patent
Gilboa et al.

(10) Patent No.: US 10,595,806 B2
(45) Date of Patent: Mar. 24, 2020

(54) FRACTIONAL FLOW RESERVE (FFR) INDEX WITH ADAPTIVE BOUNDARY CONDITION PARAMETERS

(71) Applicant: KONINKLIJKE PHILIPS ELECTRONICS N.V., Eindhoven (NL)

(72) Inventors: Guy Gilboa, Kiryat Tivon (IL); Yechiel Lamash, Haifa (IL); Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 983 days.

(21) Appl. No.: 14/059,517

(22) Filed: Oct. 22, 2013

(65) Prior Publication Data

US 2015/0112191 A1    Apr. 23, 2015

(51) Int. Cl.
*A61B 5/02* (2006.01)
*A61B 6/03* (2006.01)
*A61B 6/00* (2006.01)
*A61B 5/055* (2006.01)
(Continued)

(52) U.S. Cl.
CPC ............... *A61B 6/504* (2013.01); *A61B 6/03* (2013.01); *A61B 6/032* (2013.01); *A61B 6/5217* (2013.01); *A61B 5/026* (2013.01); *A61B 5/02007* (2013.01); *A61B 5/055* (2013.01); *G16H 50/50* (2018.01)

(58) Field of Classification Search
None
See application file for complete search history.

(56) References Cited

U.S. PATENT DOCUMENTS

| 2012/0041318 A1 * | 2/2012 | Taylor ............... A61B 5/02007 600/504 |
| 2012/0053918 A1 | 3/2012 | Taylor |
| 2012/0053921 A1 | 3/2012 | Taylor |

(Continued)

FOREIGN PATENT DOCUMENTS

WO  2014072861 A2  5/2014

OTHER PUBLICATIONS

Sharma, P., et al.; A Framework for Personalization of Coronary Flow Computations During Rest and Hyperemia; 2012; IEEE EMBS; pp. 6665-6668.

(Continued)

*Primary Examiner* — Katherine L Fernandez
*Assistant Examiner* — Colin T. Sakamoto
(74) *Attorney, Agent, or Firm* — Larry Liberchuk

(57) ABSTRACT

A method includes obtaining a boundary condition estimate. The boundary condition estimate includes at least an estimated outlet resistance of a vessel with a stenosis. The method further includes correcting the boundary condition estimate based on a severity of the stenosis, thereby creating a corrected boundary condition. The method further includes determining an FFR index based on the corrected boundary condition. The method further includes displaying the FFR index. A computing system includes a computer readable storage medium with instructions that iteratively determine at least an FFR index based on a severity of a stenosis of a vessel. The computing system further includes a computer processor that processes the instructions and generates the FFR index based on the severity of the stenosis of the vessel.

24 Claims, 3 Drawing Sheets

(51) Int. Cl.
  *A61B 5/026* (2006.01)
  *G16H 50/50* (2018.01)

(56) References Cited

U.S. PATENT DOCUMENTS

| | | | |
|---|---|---|---|
| 2012/0072190 A1 | 3/2012 | Sharma et al. | |
| 2013/0132054 A1 | 5/2013 | Sharma et al. | |
| 2013/0226003 A1 | 8/2013 | Edic et al. | |
| 2013/0246034 A1 | 9/2013 | Sharma et al. | |
| 2014/0094697 A1* | 4/2014 | Petroff | A61B 5/0066 600/427 |
| 2014/0355850 A1* | 12/2014 | Kelm | G06T 7/0012 382/128 |
| 2014/0379269 A1* | 12/2014 | Schmitt | A61B 5/6852 702/19 |

OTHER PUBLICATIONS

Chamuleau, S. A. J., et al.; Association between coronary lesion severity and distal microvascular resistance in patients with coronary artery disease; 2003; Am. J. Physiol. Heart Circ. Physiol.; 285:H2194-H2200.

Huo, Y., et al.; Intraspecific scaling laws of vascular trees; 2012; J. R. Soc. Interface; 9:190-200.

Indermuhle, A., et al.; Myocardial blood volume and coronary resistance during and after coronary angioplasty; 2011; Am. J. Physiol. Heart Circ. Physiol.; 300:H1119-H1124.

Kim, H. J., et al.; Patient-Specific Modeling of blood Flow and Pressure in Human Coronary Arteries; 2010; Annals of Biomedical Engineering; 38(10)3195-3209.

Koo, B-K, et al.; Diagnosis of Ischemia-Causing Coronary Stenoses by Noninvasive Fractional Flow Reserve Computed from Coronary Computed Tomographic Angiograms; 2011; J. of the American College of Cardiology; 58(19) 1989-1997.

Meuwissen, M., et al.; Role of Variability in Microvascular Resistance on Fractional Flow Reserve and Coronary Blood Flow Velocity Reserve in Intermediate Coronary Lesions; 2001; Circulation; 103:184-187.

Pijls, N. H. J., et al.; Fractional Flow Reserve; 1995; Circulation; 92:3183-3193.

Pijls, N. H. J., et al.; Measurement of Fractional Flow Reserve to Assess the Functional Severity of Coronary-Artery Stenosis; 1996; New England Journal of Medicine; 334(26)1703-1708.

Taylor, C. A., et al. Patient-Specific Modeling of Cardiovascular Mechanics; 2009; Annu. Rev. Biomed. Eng.; 11:109-134.

Verhoeff, B-J, et al.; Influence of Percutaneous Coronary Intervention on Coronary Microvascular Resistance Index; 2005; Circulation; 111:76-82.

* cited by examiner

FRACTIONAL FLOW RESERVE (FFR) INDEX WITH ADAPTIVE BOUNDARY CONDITION PARAMETERS

The following generally relates to the fractional flow reserve (FFR) index and more particularly to determining an FFR index using adaptive boundary conditions, and is described with particular application to computed tomography (CT). However, the following is also amenable to other imaging modalities including X-ray, magnetic resonance imaging (MRI), and/or other imaging modalities.

The FFR index is an index of the functional severity of a coronary stenosis that is calculated from pressure measurements made during coronary arteriography and is defined as the distal blood pressure (behind a stenosis) relative to the proximal pressure (close to the Ostium) under hyperaemic conditions. That is, the FFR index expresses the maximal flow down a vessel in the presence of a stenosis compared to the maximal flow in the hypothetical absence of the stenosis. The FFR value is an absolute number between 0 and 1, where a value 0.50 indicates that a given stenosis causes a 50% drop in blood pressure, and facilitates diagnosis of the extent of a stenosis.

The FFR index has been measured using a pressure wire to obtain the blood pressure before and after the stenosis. For example, during coronary catheterization, a catheter is inserted into the femoral or radial arteries using a sheath and guide wire. A sensor, affixed to the tip of the catheter, is positioned at the stenosis. The catheter and hence the sensor is pulled back and the sensor senses pressure, temperature and flow, which are recorded, across the stenosis, during conditions promoted by various agents that effect vessel geometry, compliance and resistance, and/or other characteristics. Unfortunately, this approach is costly and minimally invasive, exposing the patient to health risks.

A non-invasive approach to estimating the FFR index is through computational fluid dynamic (CFD) simulations in which blood flow and pressure through the coronaries is simulated. With this approach, the boundary conditions (i.e., resistance) outside the extracted geometry are not well-defined. One approach uses a lumped model with a constant resistor at the coronary outlets to estimate the boundary conditions. However, in actuality, this resistance is not a constant, and it does impact the FFR. As such, this approach may lead to an estimation error.

Aspects described herein address the above-referenced problems and others.

As described herein, an FFR is estimated for a vessel with a stenosis using boundary conditions. Initial boundary conditions are estimated without taking into account a severity of a vessel stenosis and used to determine an FFR. The severity is not known prior to determining the FFR. Then, the boundary conditions are corrected, iteratively, based on the determined FFR, which indicates the severity of a vessel stenosis. A final FFR is output upon satisfying stopping criterion. The final FFR will be more accurate than an FFR that does not take into account the severity of a vessel stenosis.

In one aspect, a method includes obtaining a boundary condition estimate. The boundary condition estimate includes at least an estimated outlet resistance of a vessel with a stenosis. The method further includes correcting the boundary condition estimate based on a severity of the stenosis, thereby creating a corrected boundary condition. The method further includes determining an FFR index based on the corrected boundary condition. The method further includes displaying the FFR index.

In another aspect, a computing system includes a computer readable storage medium with instructions that iteratively determine at least an FFR index based on a severity of a stenosis of a vessel. The computing system further includes a computer processor that processes the instructions and generates the FFR index based on the severity of the stenosis of the vessel.

In another aspect, a computer readable storage medium is encoded with computer readable instructions, which, when executed by a computer processor of a computing system, causes the computer processor to: estimate an outlet resistance boundary condition estimate for a vessel with a stenosis based on a geometry of the vessel and a flow parameter of the vessel, iteratively correct the boundary condition estimate based on a severity of the stenosis; and determine an FFR index based on the corrected boundary condition.

The invention may take form in various components and arrangements of components, and in various steps and arrangements of steps. The drawings are only for purposes of illustrating the preferred embodiments and are not to be construed as limiting the invention.

FIG. 1 schematically illustrates a computing system, which is configured to determine at least an FFR index, in connection with an imaging system.

The following describes an iterative approach for determining an FFR index. This approach includes initially assuming all vessels are healthy and using a CFD simulation with a resistance boundary condition estimate to determine an FFR index. Then, the resistance boundary condition is iteratively corrected according to the stenosis severity, which is estimated by the FFR index from the previous iteration. A subsequent FFR index is then determined based on the corrected boundary condition. The iterative process of correcting resistance boundary condition and calculating another FFR index continues until stopping criterion is satisfied. A final FFR index is then output.

Figure 1:
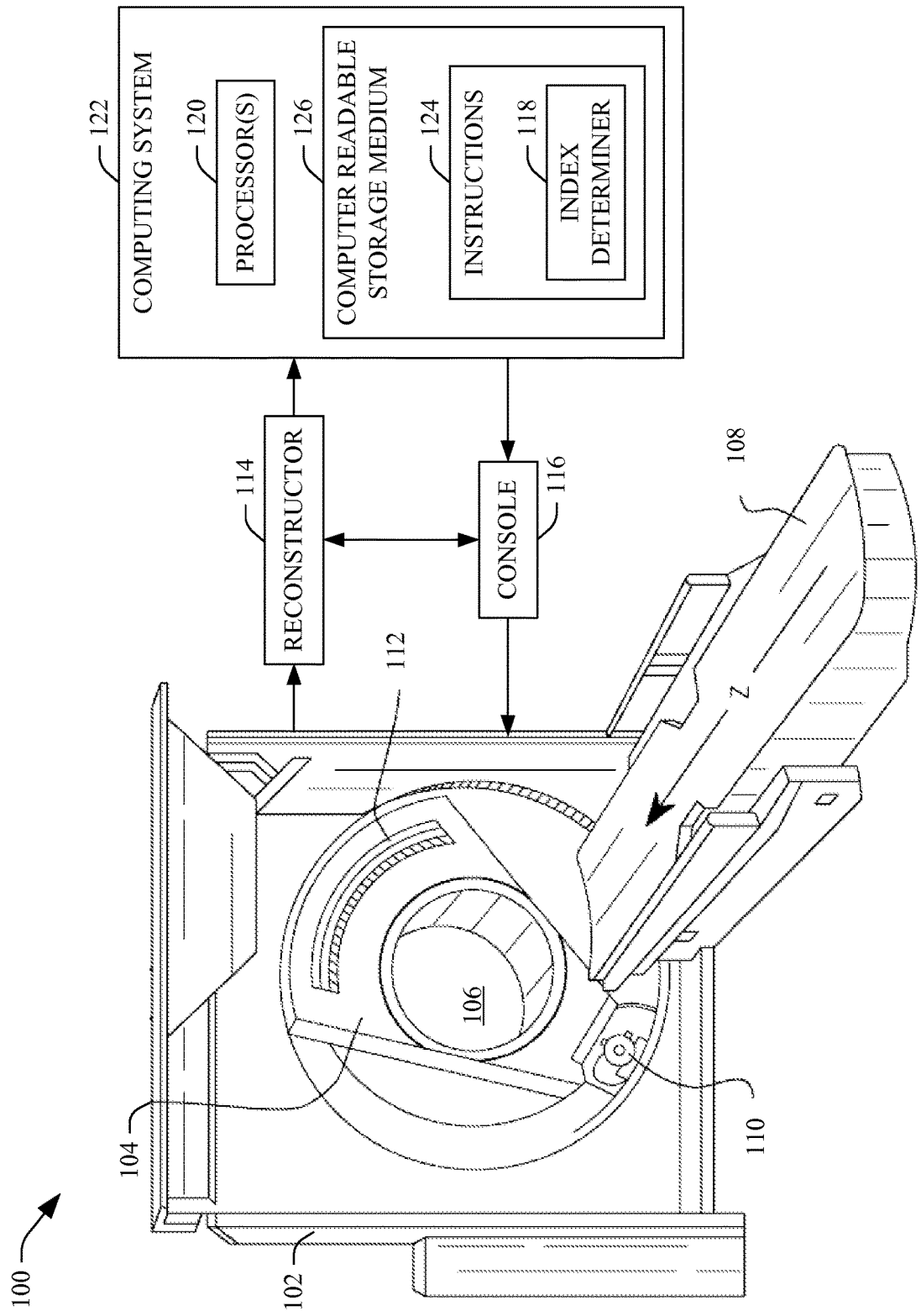

FIG. 1 schematically illustrates an imaging system 100 such as a CT scanner. The imaging system 100 includes a generally stationary gantry 102 and a rotating gantry 104, which is rotatably supported by the stationary gantry 102 and rotates around an examination region 106 about a z-axis. A subject support 108, such as a couch, supports an object or subject in the examination region 106.

A radiation source 110, such as an x-ray tube, is rotatably supported by the rotating gantry 104, rotates with the rotating gantry 104, and emits radiation that traverses the examination region 106. A radiation sensitive detector array 112 subtends an angular arc opposite the radiation source 110 across the examination region 106. The radiation sensitive detector array 112 detects radiation traversing the examination region 106 and generates a signal indicative thereof for each detected photon.

A reconstructor 114 reconstructs the projection, generating volumetric image data indicative of a scanned portion of a subject or object located in the examination region 106. A general-purpose computing system or computer serves as an operator console 116. The console 116 includes a human readable output device such as a monitor and an input device such as a keyboard, mouse, etc. Software resident on the console 116 allows the operator to interact with and/or operate the scanner 100 via a graphical user interface (GUI) or otherwise.

An index determiner 118 is configured to at least process image data representing a vessel(s) (e.g., coronary arteries, cerebral artery, etc.) with a stenosis and determine an FFR index. As described in greater detail below, in one non-limiting instance, the index determiner 118 uses an iterative approach to correct an initial boundary conditions estimate (e.g., resistance) based on a severity of a stenosis. As a result, inaccuracy from an FFR estimation that does not iteratively correct the boundary conditions, such as an FFR estimation that utilizes a lumped model with a constant resistance at the coronary outlets, can be mitigated.

In the illustrated example, the index determiner 118 is implemented with one or more computer processors 120 (e.g., a central processing unit or CPU, a microprocessor, etc.), of a computing system 122, that execute one or more computer readable instructions 124 stored in one or more computer readable storage mediums 126 (which excludes transitory medium) such as physical memory and/or other non-transitory storage medium. The processor(s) 120 may additionally or alternatively execute one or more computer readable instructions carried by a carrier wave, a signal and/or other transitory medium.

Figure 2:
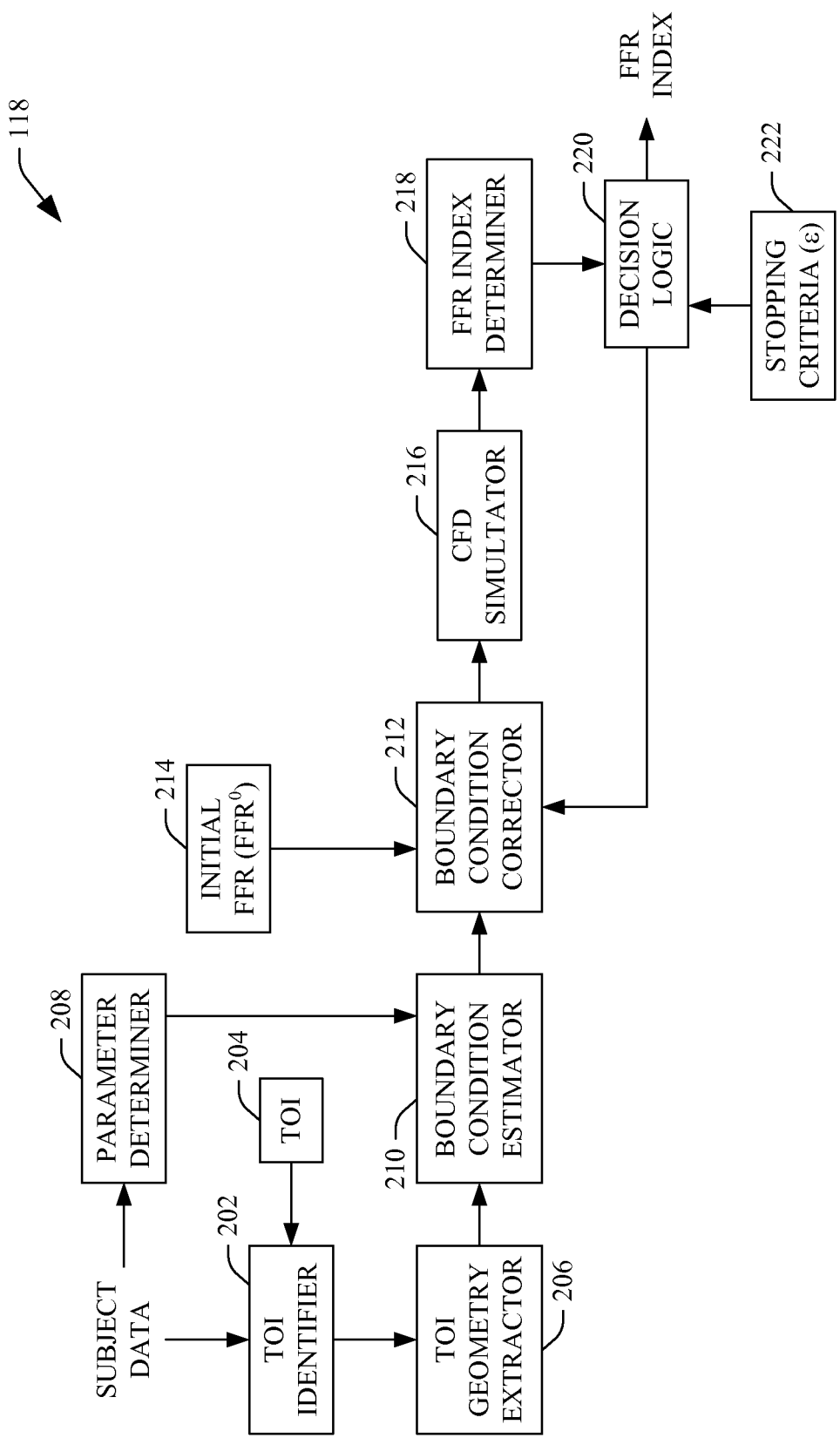
FIG. 2 illustrates an example of an index determiner of FIG. 1.

FIG. 2 illustrates an example of the index determiner 118.

A tissue of interest (TOI) identifier 202 obtains, as input, subject data, including image data representative of tissue of interest (TOI) 204 and identifies the tissue of interest 204 in the image data. The tissue of interest 204 can be predetermined or identified by a signal indicative of a user selected tissue of interest, a default tissue of interest, etc. The TOI identifier 202 can employ automatic and/or manual approaches to identify the tissue of interest. An example of tissue of interest is tubular tissue such as a vessel with a stenosis.

A TOI geometry extractor 206 extracts geometrical information from the identified tissue of interest. The TOI identifier 202 can employ automatic and/or manual approaches to extract the geometrical information. By way of example, the extraction may include employing segmentation with active-contours and level-sets tuned for coronary vessels where the tissue of interest is the coronary vessels, followed by optional additional manual editing to produce high quality segmentation. From this and/or other extraction, an effective diameter at the ostium $D_o$ and/or other tissue geometry can be determined.

A parameter determiner 208 determines at least one parameter based on the subject data. For example, in the context of vessel stenosis, the parameter determiner 208 can determine an inlet flow-rate $Q_o$ (i.e., flow rate at the ostium). This can be achieved based on subject data such as weight, body mass index (BMI), gender, age, blood test results, anatomical imaging data (e.g., myocardium mass and estimated stroke-volume), and/or subject data.

A boundary condition estimator 210 estimates at least one boundary condition (e.g., flow rate Q, average velocity, resistance, etc. of vessel outlets) based on the geometry extracted (e.g., diameter at the ostium $D_o$) by the TOI geometry extractor 206 and the parameter determined (e.g., the inlet flow-rate $Q_o$) by the parameter determiner 208. The boundary condition estimator 210 can estimate the boundary, as described in application Ser. No. 61/722,814, filed on Nov. 6, 2012, and entitled "FRACTIONAL FLOW RESERVE (FFR) INDEX," the entirety of which is incorporated herein by reference.

A boundary condition corrector 212 corrects the resistance boundary condition based on EQUATION 1:

$$R^i = R^{i-1} * C(FFR^{i-1}),\qquad \text{EQUATION 1:}$$

where $R^i$ is a current outlet resistance, $R^{i-1}$ is a previously determined outlet resistance, and $C(FFR^{i-1})$ is a correction factor. The correction factor C is a known function (or look-up-table) and is defined for all $0<FFR<=1$ and monotonically decreases and assumes the value $C(1)=1$, so a perfectly healthy vessel attains the resistance $R^{i-1}$. For the first iteration, or $i=1$, the boundary condition corrector 212 utilizes an initial FFR 214, which, in this example, is $FFR^0=1$.

A CFD processor 216 performs a computational fluid dynamic (CFD) simulation, for example, using partial-differential-equations. Generally, CFD is a fluid mechanics approach that uses numerical methods and/or algorithms to solve and analyze problems that involve fluid flows. The CFD processor 216 performs the calculations with surfaces defined by boundary conditions determined by the boundary condition corrector 212. However, other boundary conditions can also be employed. The output, in one instance, includes full volumetric information of pressure and velocity at all points.

An FFR index determiner 218 determines an FFR index based on the CFD results. This includes determining the FFR index based on the corrected boundary conditions. Suitable approaches to determine an FFR index using computational fluid dynamics is described in, but not limited to, Taylor C A, Figueroa C A, "Patient-Specific Modeling of Cardiovascular Mechanics," Annual Review of Biomedical Engineering, Vol. 11: 109-134, August 2009, and Huo Y, Kassab G S, "Intraspecific scaling laws of vascular trees," *J. R. Soc. Interface*, 15 Jun. 2011.

Decision logic 220 determines whether another iteration is performed. Stopping criteria 222 is set, for example, to a small constant $\varepsilon \ll 1$, which defines the tradeoff between accuracy (low value) and convergence time (high value). In one instance, $\varepsilon \approx 0.01$. In a variation, the stopping criterion 222 alternatively or additionally includes a predetermined amount of time. The decision logic 218 compares the current $FFR^i$ index with the previous $FFR^{i-1}$ index. If $|FFR^i - FFR^{i-1}| < \varepsilon$ then the current $FFR^i$ is set as the final FFR index. Otherwise, $i=i+1$, and a next iteration is performed for $i=i+1$.

The initial FFR of $FFR^0=1$ assumes, for a first iteration, that all vessels are healthy. However, if a vessel is not healthy, this will be detected after the first simulation, as the simulated resistance will be lower than what it should be (i.e., unhealthy vessels have higher resistance). Therefore, the FFR of the first iteration will show exaggerated low FFR values, which will be corrected in later iterations. If the vessel is healthy, then the assumption is true, and the CFD should produce realistic results.

For example, $R^i$, for $i=1$ with $FFR^0=1$ and $C(1)=1$, using Equation 1, is $R^0$. If the vessel is unhealthy, this $R^i$ will be higher than it should be. As a result, the computation of the next FFR, i.e., $FFR^1$, with $R^1=R^0$ will result in a difference ($|FFR^1-FFR^0|$) that is much greater than E and another iteration will be performed. In the next iteration, $i=2$, $R^2$, using Equation 1 and based on $FFR^1$ which is less than 1, will be less than $R^0$ and closer to the actual resistance. The computation of the next FFR, i.e., $FFR^2$, with $R^2$ will result in a difference ($|FFR^2-FFR^1|$) that is smaller than ($|FFR^1-FFR^0|$).

However, if the vessel is healthy, $R^i$, for $i=1$, will be close to the actual resistance based on the assumption, and $|FFR^1-FFR^0|$ will be less than E and another iteration will not be performed; another iteration is performed only if $|FFR^2-FFR^1|$ is larger than E. Thus, an incorrect initial assumption of a healthy vessel will be detected based on the difference between the FFR computed based on the initial assumption and the next determined FFR and will be corrected through performing one or more subsequent iterations.

The FFR index can be displayed, stored, conveyed to another device, etc.

The particular adaptive (pressure/FFR dependent) resistance model employed is not limited to that discussed above. A general approximation to the FFR index is shown in EQUATION 2:

$$FFR = \frac{R}{R+r},\qquad \text{EQUATION 2}$$

where R and r denote the microvascular and stenosis resistances respectively. Here, R is combined venues resistance with the larger micro arteriolar resistance.

Figure 3:
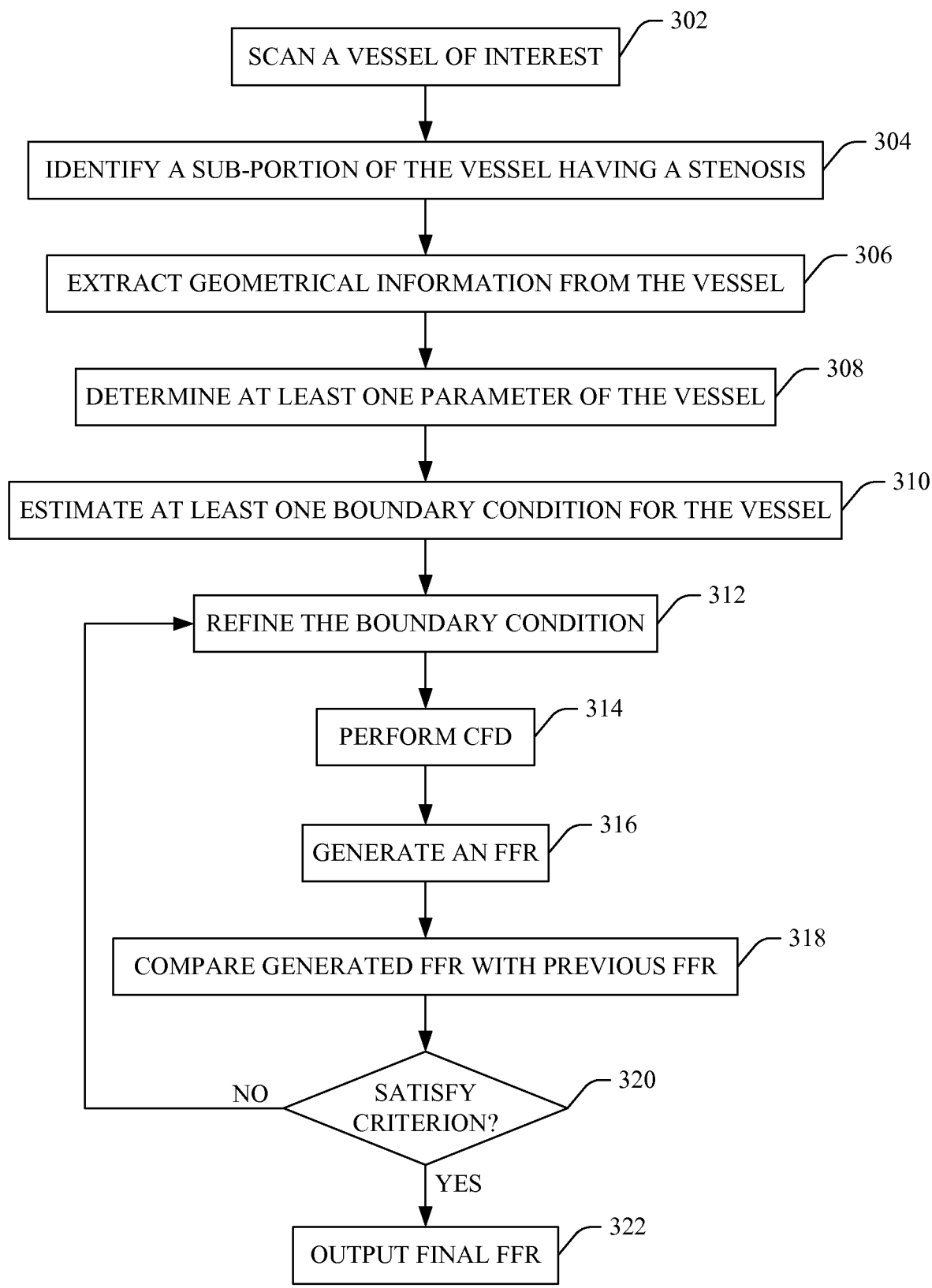
FIG. 3 illustrates an example method for determining an FFR index.

FIG. 3 illustrates an example method for determining an FFR index.

At 302, a vessel of interest of a subject is scanned.

At 304, a sub-portion of the vessel having a stenosis is identified in the image data from the scan.

At 306, geometrical information, such as a diameter, a radius, etc., is extracted from the vessel.

At 308, at least one property such as inlet flow-rate, etc. of the vessel is determined.

At 310, at least one boundary condition (e.g., resistance) for the vessel is estimated, e.g., based on the extracted geometrical information and the at least one parameter.

At 312, the boundary condition is refined based on a previous FFR index. For a first iteration, the previous FFR index is set to an initial FFR index, which assumes all vessels are healthy. For each subsequent iteration, the previous FFR index is the corresponding generated preceding FFR index.

At 314, a computational fluid dynamic (CFD) simulation is performed based on the refined boundary condition.

At 316, a current FFR index is generated based on a result of the CFD.

At 318, the current FFR index is compared with a previous FFR index.

Likewise, for the first iteration, the previous FFR index is set to an initial FFR index, which assumes all vessels are healthy, and, for each subsequent iteration, the previous FFR index is the corresponding generated succeeding FFR index.

At 320, if a difference between the current FFR index and the previous FFR index does not satisfy stopping criterion, then acts 312-318 are repeated.

If at 320, the difference between the current FFR index and the previous FFR index satisfies the stopping criterion, the current FFR index is output at 322 as the final FFR index.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium. It is to be appreciated that the ordering of the above acts is not limiting. As such, other orderings are contemplated herein. In addition, one or more acts may be omitted and/or one or more additional acts may be included.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof

The invention claimed is:

1. A method, comprising:
    obtaining with a processor, a boundary condition estimate, wherein the boundary condition estimate includes at least an estimated outlet resistance of a vessel with a stenosis from medical image data representing the vessel with the stenosis;
    obtaining, with the processor, an initial fractional flow reserve (FFR) index, wherein the initial FFR index includes the boundary condition estimate and assumes the vessel with the stenosis is healthy;
    employing, with the processor, a first correction factor to correct the boundary condition estimate, wherein the first correction factor is a function of the initial FFR index, monotonically decreases, and is bounded by 0<FFR≤1, thereby creating a first corrected boundary condition estimate;
    determining, with the processor, a first iteration FFR index based on the first corrected boundary condition estimate; and
    displaying, with the processor, the first iteration FFR index.

2. The method of claim 1, wherein using the first correction factor to correct the boundary condition estimate is iterative.

3. The method of claim 2, further comprising:
    performing a first computational fluid dynamics (CFD) simulation using the first corrected boundary condition estimate; and
    generating the first iteration FFR index based a result of the first CFD simulation.

4. The method of claim 3, wherein the first correction factor is one of a function or a look up table.

5. The method of claim 3, wherein the first correction factor is defined for all 0<FFR<=1.

6. The method of claim 3, wherein, for the first iteration FFR index, the initial FFR index is a predetermined initial condition with a value of 1.

7. The method of claim 6, further comprising:
    comparing the initial FFR index with the value of 1 to the first iteration FFR index;
    using a second correction factor, wherein the second correction factor is a function of the first iteration FFR index, to correct the first corrected boundary condition estimate, thereby creating a second corrected boundary condition estimate, in response to a difference between the initial FFR index with the value of 1 and the first iteration FFR index is greater than a predetermined threshold value; and
    determining a second iteration FFR index based on the second corrected boundary condition.

8. The method of claim 3, wherein, for a subsequent iteration FFR index, the FFR index of a previous iteration is the FFR index for the immediately preceding iteration.

9. The method of claim 7, further comprising:
    comparing the first iteration FFR index with the second iteration FFR index;
    using a third correction factor, wherein the third correction factor is a function of the second iteration FFR index, to correct the second corrected boundary condition estimate, thereby creating a third corrected boundary condition estimate, in response to a difference between the first iteration FFR index and the second iteration FFR index is greater than a predetermined threshold value; and determining a third iteration FFR index based on the third corrected boundary condition.

10. The method of claim 7, further comprising:
performing a second CFD simulation using the second corrected boundary condition estimate; and
generating the second iteration FFR index based a result of the second CFD simulation.

11. The method of claim 10, further comprising:
comparing the second iteration FFR index with the first iteration FFR index; using a second correction factor, wherein the second correction factor is a function of the second iteration FFR index, to correct the second corrected boundary condition estimate, thereby creating a third corrected boundary condition estimate, in response to a difference between the second iteration FFR index and the second iteration FFR index is greater than a predetermined threshold value; and
determining a third iteration FFR index based on the third corrected boundary condition estimate.

12. The method of claim 7, further comprising:
setting the first iteration FFR index equal to the initial iteration FFR index in response to the difference between the initial iteration FFR index and the first iteration FFR index is less than the predetermined threshold value.

13. The method of claim 1, further comprising:
estimating the boundary condition estimate based on a geometry of the vessel and flow parameter of the vessel.

14. The method of claim 1, wherein the boundary condition estimate is a resistance boundary condition, and the first corrected boundary condition estimate is determined from the following:

$$R^i = R^{i-1} * C(FFR^{i-1}),$$

where $R^i$ is a current outlet resistance of a vessel, $R^{i-1}$ is a previously determined outlet resistance of the vessel, and $C(FFR^{i-1})$ is the correction factor.

15. The method of claim 14, wherein the correction factor has a value of one when a value of the $FFR^{i-1}$ is one.

16. The method of claim 14, wherein a $FFR^{i-1}$ value of one corresponds to a healthy vessel.

17. The method of claim 14, wherein a $FFR^{i-1}$ value of less than one corresponds to an unhealthy vessel.

18. The method of claim 14, wherein the value of $FFR^{i-1}$ is set to a value of one for i=1.

19. The method of claim 18, wherein an $FFR^{i-1}$ value for i=2 is less than one.

20. The method of claim 1, wherein the initial FFR is set to a value of one.

21. The method of claim 20, wherein the first iteration FFR index is equal to one for a healthy vessel.

22. The method of claim 21, wherein the first iteration FFR index is less than one for an unhealthy vessel.

23. The method of claim 22, wherein a second iteration FFR index is less than the first FFR index.

24. The method of claim 1, wherein the boundary condition estimate is a resistance boundary condition.

* * * * *